United States Patent [19]

Takano et al.

[11] Patent Number: 4,547,343
[45] Date of Patent: Oct. 15, 1985

[54] STERILIZER

[75] Inventors: Motoharu Takano; Masaru Sugimura; Keiichi Kushima, all of Tokyo; Atae Ezaki, Saitama, all of Japan

[73] Assignee: Q. P. Corporation, Tokyo, Japan

[21] Appl. No.: 475,213

[22] Filed: Mar. 14, 1983

[30] Foreign Application Priority Data

Apr. 16, 1982 [JP] Japan .................................. 57-63582
Oct. 8, 1982 [JP] Japan ................................. 57-177283
Oct. 29, 1982 [JP] Japan ................................. 57-190480

[51] Int. Cl.⁴ .......................... A23B 7/06; A61L 3/00
[52] U.S. Cl. ..................................... 422/304; 99/362; 198/803.01; 414/417; 422/302; 426/407
[58] Field of Search ................... 422/303, 304, 302; 426/396, 407, 413; 414/417; 99/360, 362; 198/648, 472; 220/21

[56] References Cited

U.S. PATENT DOCUMENTS

| 3,165,055 | 1/1965 | Van der Winden | 99/362 |
| 3,186,586 | 6/1965 | Box | 220/21 X |
| 3,528,826 | 9/1970 | Wilson | 99/362 X |
| 3,537,382 | 11/1970 | Hoellenkamp | 99/362 |
| 3,780,892 | 12/1973 | Frank | 414/417 X |
| 3,863,789 | 2/1975 | Hunter et al. | 198/472 X |
| 3,927,976 | 12/1975 | Reimers et al. | 426/407 X |
| 3,972,679 | 8/1976 | Ruig | 422/304 X |
| 3,986,832 | 10/1976 | Smorenburg | 422/304 X |
| 4,385,035 | 5/1983 | Akitoshi et al. | 422/304 X |
| 4,408,549 | 10/1983 | Quarnström | 414/417 X |

Primary Examiner—Barry S. Richman
Assistant Examiner—B. P. Heaney
Attorney, Agent, or Firm—Browdy and Neimark

[57] ABSTRACT

A sterilizer which has two transfer chains moving through sterilizing and cooling tanks; open-backed transfer containers with holes in their walls and locking members at both ends, which are supported between the chains; and inner vessels containing the materials being treated, which have holes in the walls thereof and locking means, which are engageable with the locking members, at both ends thereof, and which are adapted to be removably inserted into the containers. Projections extend inward from the circumferential edges of the holes in the walls of the containers and/or inner vessels, serving to support the materials and define liquid passages between the materials and the inner surfaces of the containers and/or inner vessels. Two front intermittent driving wheels and two rear intermittent driving wheels are provided in an inner vessel insertion and discharge section, the chains are wrapped around these wheels so that the parts of the chains which are in front of the front wheels, behind the rear wheels, and between the front and rear wheels hang loosely, an insertion means provided at one side of the front wheels fits the inner vessel from a material feed means into a container supported on the front wheels, a discharge means provided at one side of the rear wheels forces the inner vessel out of the container supported on the rear wheels onto a treated material removal means, and inner vessel guide members for guiding the inner vessels into the transfer containers are provided between the feed means and the front wheels, and between the removal means and the rear wheels, and which are adapted to move pivotally to horizontal positions only when a inner vessel is being inserted into or discharged from a container.

6 Claims, 9 Drawing Figures

STERILIZER

BACKGROUND OF THE INVENTION

1. Field of the Invention

This invention relates to an improvement in a continuous sterilizer.

2. Description of the Prior Art

One conventional sterilizing system has right and left transfer chains circulated in a high-pressure sterilizer, and transfer containers supported between the transfer chains and housing therein materials being treated, the materials being thus transferred and sterilized continuously. In this sterilizing system, it is necessary that covers of the transfer containers are opened and closed every time materials are inserted thereinto and withdrawn therefrom. Namely, the operations for inserting materials into, and withdrawing materials from, the transfer containers are very time-consuming. Moreover, insufficiently protected materials, such as materials packed in inadequate bags, are damaged during the material insertion and withdrawal operations, and smaller materials can move in the containers while they are being transferred, and can be damaged in this way also.

Another sterilizing system, in which vessels containing the materials being treated are withdrawably housed in transfer containers so that the materials are sterilized as they are transferred, is known from Japanese Patent Laid-open No. 2669/1982. In this system, the transfer containers are first separated from a sterilizer so that the vessels containing the materials being treated can be housed therein, and the transfer containers are then returned to the sterilizer. Therefore, the structure of this system is very complicated, and the operation thereof is time-consuming.

Furthermore, when the materials being treated are placed in a vessel, they are in close contact with the inner surface of the latter, so that the hot water or cooling water is not spread uniformly and speedily over each part of the materials. This causes a reduction in the thermal sterilizing and cooling efficiencies, and the materials are left in an unevenly heat-treated state. When materials inserted in a certain type of pouch (bag or dish), are sterilized, burns are left on the portion of the pouch which touchs the inner surface of the inner vessel in which the pouch is housed.

SUMMARY OF THE INVENTION

The present invention has been developed with a view to eliminating the above drawbacks encountered in conventional sterilizers.

A first object of the present invention is the provision of a sterilizer comprising a pair of transfer chains circulated in a sterilizer body, a plurality of transfer containers, each of which is supported on the transfer chains, and each of which has an opening at one side thereof, and a plurality of inner, open-topped vessels, each of which contains therein materials being treated, and each of which is adapted to be inserted into and discharged from a transfer container through the opening thereof by a single button-pressing operation, the materials being treated being thereby inserted into and discharged from the transfer containers easily and speedily, and also inserted into and discharged from the inner vessels simply via the openings at the upper ends thereof, permitting the sterilizing operation to be carried out efficiently.

A second object of the present invention is the provision of a sterilizer as described above, wherein the materials being treated, which are placed in each of the inner vessels, are supported on projections formed on the inner edges of each of a plurality of through holes provided in the walls thereof, the sterilizing hot water and the liquid for cooling the sterilized materials being thereby spread speedily and uniformly through liquid passages formed between the projections and the inner surface of the inner vessel, so as to improve the sterilizing and cooling efficiencies to a great extent.

Hot water for heat sterilization is usually heated to a temperature which is 5° to 10° C. higher than the temperature required for sterilization. According to the present invention, the materials being treated are supported by projections of through holes of the inner vessels, and liquid passages are formed between the materials and the wall surfaces of each inner vessel, enabling the hot water to exhibit a good heat-exchange efficiency. Therefore the hot water need not be heated to a temperature which is 5° to 10° C. higher than the sterilization temperature. This helps prevent the surfaces of the containers, made of polyethylene or the like, from being excessively heated and damaged or from receiving net-like patterns that would damage their appearance. The projections also prevent the displacement of the materials while they are being transferred. The projections also prevent pouches of polyethylene, which contain the materials being treated, from coming into full contact with the inner surfaces of the inner vessel.

A third object of the present invention is the provision of a sterilizer as described above, wherein the right and left transfer chains are wrapped around a pair of front intermittent driving wheels and a pair of rear intermittent driving wheels, the portions of each of the transfer chains which are in front of the front driving wheels, behind the rear driving wheels, and between the front and rear driving wheels hanging loosely to enable the transfer containers to stop when they reach the upper parts of the intermittent driving wheels, the inner vessels containing the materials being inserted into or discharged from the transfer containers when the transfer containers are temporarily stopped, the insertion and discharge of the inner vessels into and from the transfer containers being done simply and reliably when the transfer containers are stopped at these positions although the sterilizing operation is carried out continuously without being stopped, so that the sterilizing operation can be operated continuously at a high efficiency.

A fourth object of the present invention is the provision of a sterilizer as described above, wherein the sterilizer includes an insertion means and a discharge means for inserting and discharging the inner vessels into and from the transfer containers, the insertion means and the discharge means being provided at one side of the front and rear pairs, respectively, of intermittent driving wheels, each of the inner vessels being thereby inserted into and discharged from a transfer container smoothly via an opening at one side thereof, the construction of the sterilizer being thereby simplified.

Another object of the present invention is the provision of a sterilizer as described above, wherein the sterilizer includes guide members for the inner vessels, the guide members being provided between the inner vessel insertion means and a transfer container stopped on one pair of intermittent driving wheels, and between the inner vessel discharge means and another transfer container stopped on the other pair of intermittent driving wheels, the guide members falling into position only when the inner vessels are being inserted into and discharged from the transfer containers, the guide members normally standing erect so as not to hamper the transfer container-feeding operation, the operation of inserting and discharging the materials being treated into and from the transfer containers being thereby carried out more smoothly and reliably.

The above and other objects as well as advantageous features of the invention will become apparent from the following description of the preferred embodiment taken in conjunction with the accompanying drawings.

DESCRIPTION OF THE PREFERRED EMBODIMENT

Figure 1:
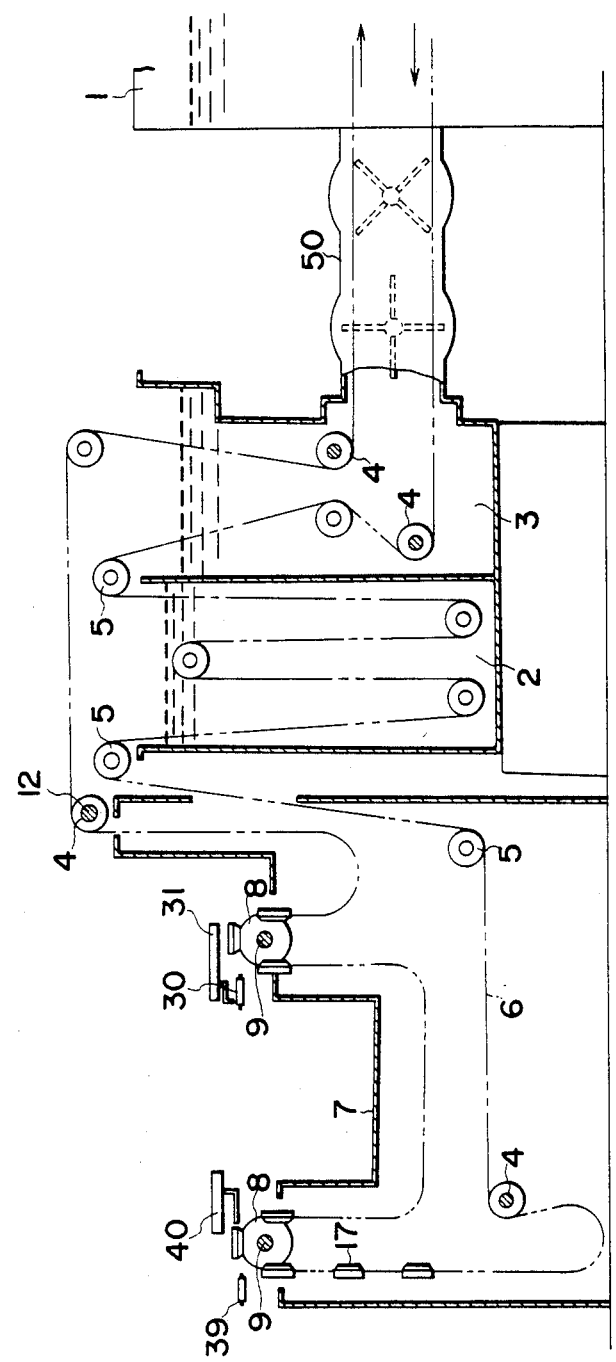
FIG. 1 is a partially cutaway front elevation of a sterilizer according to the present invention.

An embodiment of the present invention will now be described with reference to the drawings. Each of right and left transfer chains 6 which are arranged so as to be circulated through a high-pressure sterilizing tank 1 and cooling tanks 2, 3 by driving wheels 4 and guide wheels 5, is wrapped partly around one each of pairs of intermittent driving wheels 8 provided in front of and behind a frame 7 at one side of a cooling tank unit, in such a manner that the parts of the chain 6 which are in front of the front driving wheel 8, behind the rear driving wheel 8, and between these driving wheels 8 hang loosely. The driving wheels 8 are turned intermittently in synchronism with the driving wheels 4 so that the transfer chains 6 are stopped intermittently at the driving wheels 8.

Figure 2:
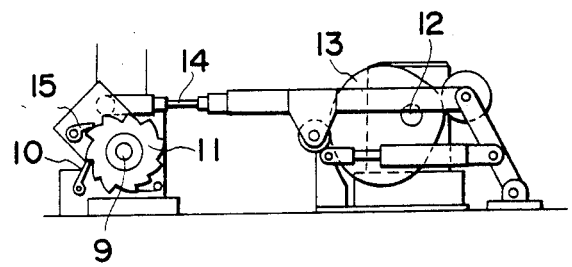
FIG. 2 is a front elevation of the intermittent driving means for the intermittent driving wheels.
Figure 5:
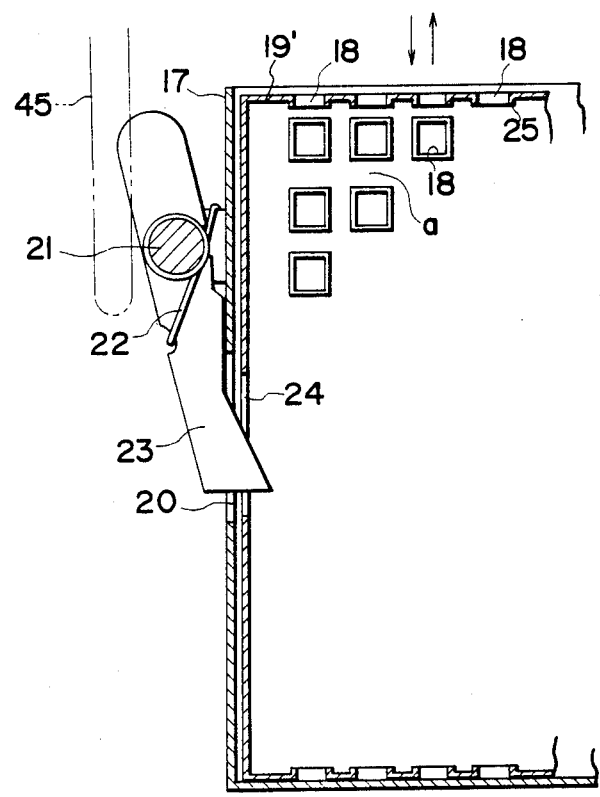
FIG. 5 is horizontal cross section of a transfer container of the present invention, with an inner vessel inserted therein.
Figure 3:
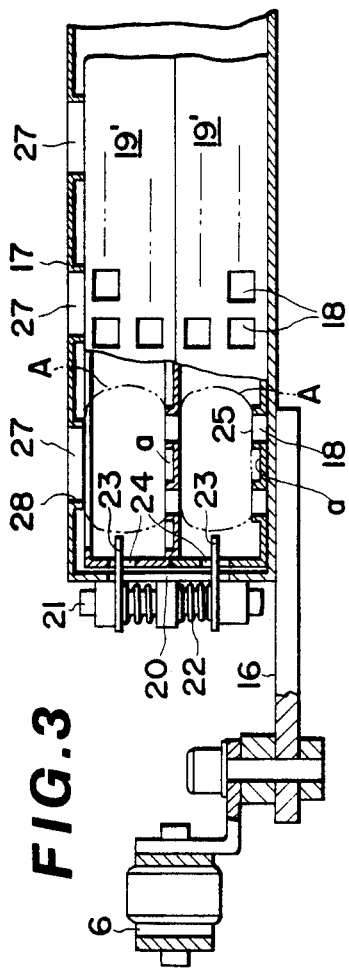
FIG. 3 is a partially cutaway side elevation illustrating a transfer container used in the present invention, into which an inner vessel has been inserted.
Figure 4:
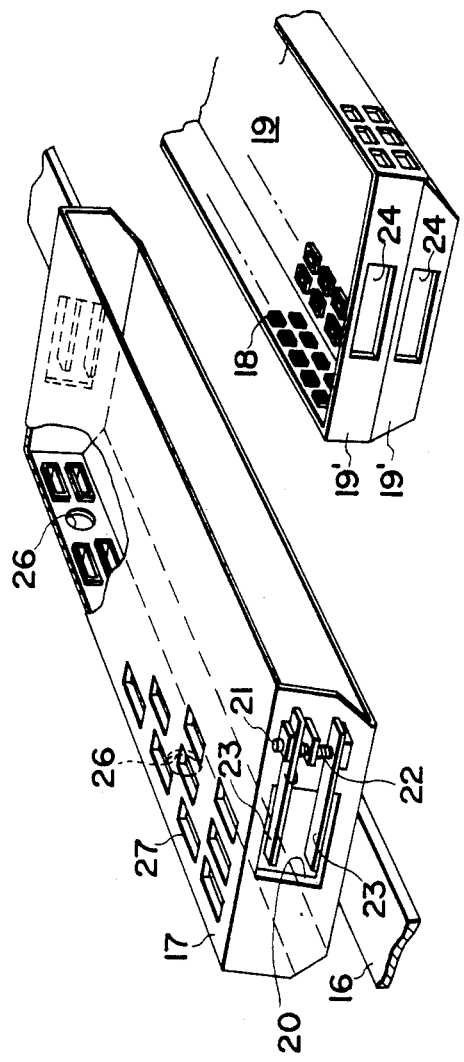
FIG. 4 shows perspective views illustrating the transfer container and inner vessel used in the present invention, when separated.
Figure 6:
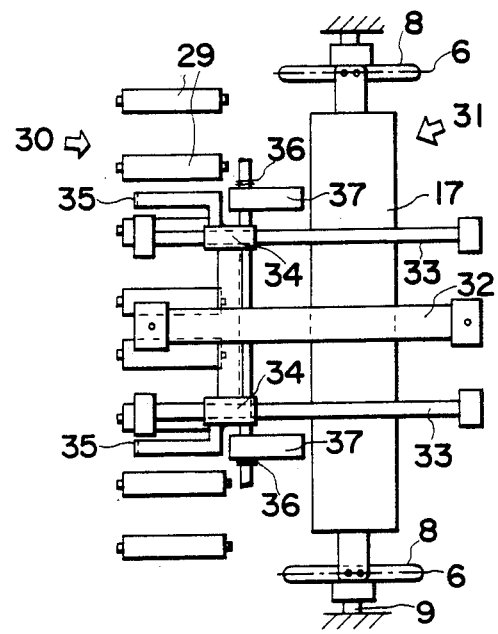
FIG. 6 is a plan view of the inner vessel insertion unit of the present invention.
Figure 7:
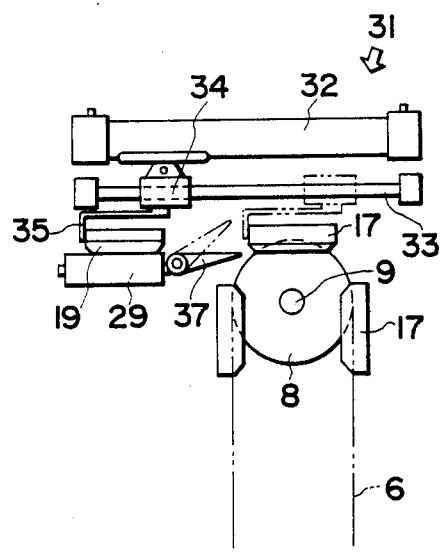
FIG. 7 is a front elevation of the inner vessel insertion unit of the present invention.
Figure 8:
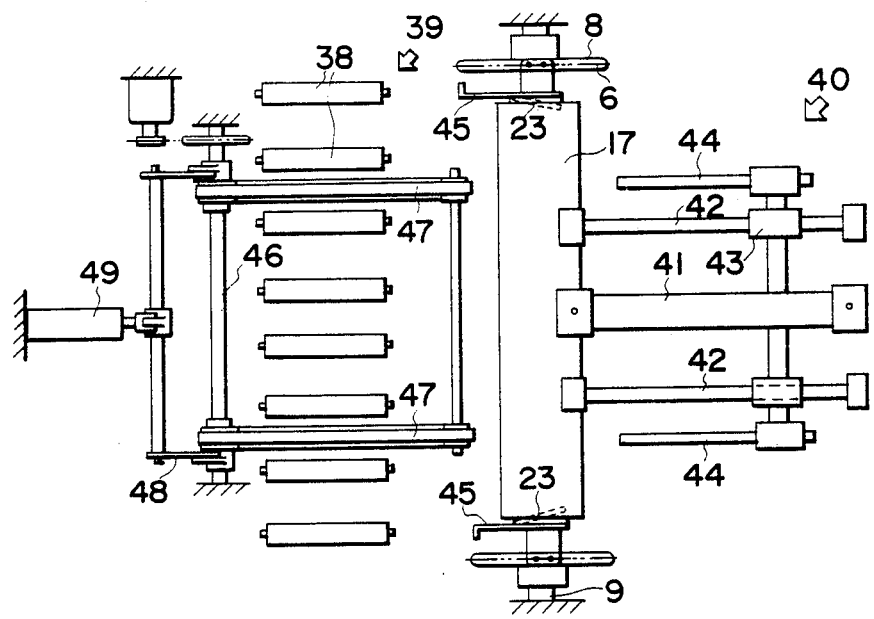
FIG. 8 is a plan view of the inner vessel discharge unit of the present invention.
Figure 9:
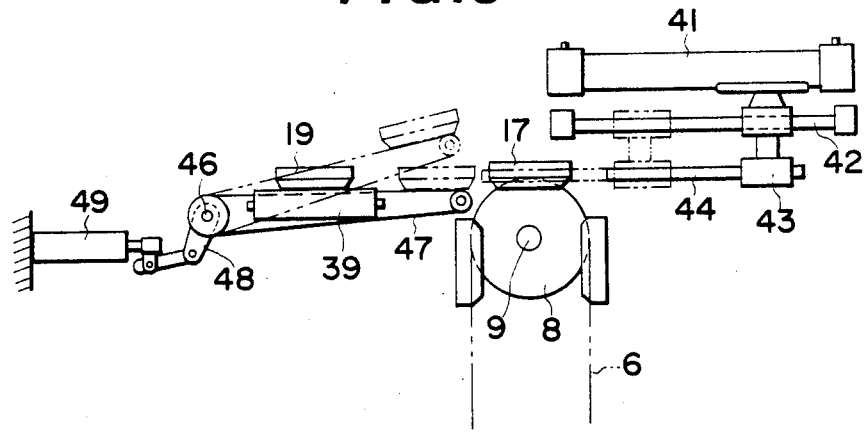
FIG. 9 is a front elevation of the inner vessel discharge unit of the present invention.

FIG. 2 shows an example of an intermittent driving means for the driving wheels 8. A ratchet 11, the reverse rotation of which is prevented by a pawl 10, is mounted on a shaft 9 of intermittent driving wheels 8. A feed pawl 15 at the free end of a feed lever 14, which is actuated by a cam 13 mounted on a shaft 12 of the driving wheels 4, engages with the ratchet 11. Thus the driving wheels 8 can be turned intermittently in synchronism with the driving wheels 4.

A transfer container 17, having two longitudinal end walls, a top and a bottom wall a lateral side wall and an open lateral side at the rear side thereof and having a plurality of holes in the walls thereof, is supported between the right and left transfer chains 6 by a mounting member 16. An inner vessel 19 having a plurality of through holes 18 and adapted to contain the materials being treated fits removably into the tranfer container 17 through the opening thereof. The transfer container 17 is provided with windows 20 in both end walls thereof, and support shafts 21 each supported on part of the outer surfaces of these end walls, at one side of each of the windows 20. Resilient locking members 23 on each of the support shafts 21, inwardly urged by a spring 22, engage via the window 20 with a locking means in the form of locking holes 24 provided in the inner vessel 19. The inner vessel 19 is thus combined unitarily with the transfer container 17.

The inner vessel 19 has two longitudinal end walls, two lateral side walls, a bottom wall and an open top and could either be a single top-opened box or a plurality of smaller inner vessel members 19', 19', which are joined together to form a single inner vessel. The circumferential edge of each of the through holes 18 is a projection 25 which is formed by punching through the wall of the inner vessel 19 in the inward direction. The projections 25 are adapted to support the materials A being treated and form a liquid flow passage a between the materials A and the inner surfaces of the inner vessel.

The front wall of the transfer container 17, i.e. the wall of the transfer container 17 which is on the opposite side of the opening thereof, is provided with right and left through holes 26, into which pushers, which will be described later, can be inserted. Each of holes 27 provided in a top wall of the transfer container 17 also has a projection 28 extending in the inward direction. The bases of the transfer container 17 and inner vessel 19 are shaped substantially like the bottom of a ship, so that the inner vessel 19 can be easily inserted into and discharged from the transfer container 17.

A feed means 30 consisting of driving rollers 29 is positioned behind the front intermittent driving wheels 8. An insertion means 31 adapted to place an inner vessel, which has been positioned on the feed means 30, into transfer container 17 is provided in the vicinity of the front intermittent driving wheels 8. The insertion means 31 consists of an air cylinder 32, slide blocks 34 actuated by the air cylinder 32, slide blocks 34 actuated by the air cylinder 32 and guided by guide rods 33, and a pair of locking rods 35 provided on the slide blocks 34. A pair of guide plates 37, the free ends of which are urged by spring 36 so as to move pivotally in the upward direction, are supported on a shaft between the front intermittent driving wheels 8 and the feed means 30. The guide plates 37 are normally at the upper positions of their pivotal movements, to enable the transfer containers to be moved in an arc by the transfer chains 6. The guide plates 37 are adapted to fall down by their own weights only when an inner vessel 19 is being fitted into a transfer container 17. Thus an inner vessel 19 can be fitted into its transfer container 17 smoothly.

A removal means 39 positioned behind the rear driving wheels 8 and consisting of driving rollers 38, and a discharge means 40 adapted to force the inner vessel 19 out of the transfer container 17, which is on the rear intermittent driving wheels 8, onto the removal means 39 are provided in the vicinity of the rear intermittent driving wheels 8. The discharge means 40 consists of an air cylinder 41, slide blocks 43 actuated by the air cylinder 41 and guided by guide rods 42, and a pair of pushers 44 provided on the slide blocks 43. Unlocking members, in the form of release guides 45, which are adapted to press the outer ends of the locking pawls 23 of the transfer container 17 to disengage and unlock the locking pawls 23 from the locking holes 24, are provided on the inner sides of the rear intermittent driving wheels 8.

A pair of guide belts 47 are provided so as to extend from a shaft 46, which is provided on the outer side of the removal means 39, in the forward direction through spaces between the driving rollers 38. The guide belts 47 are so formed that they can be moved pivotally in the upward direction or to a horizontal position by arm levers 48, which are moved about the shaft 46 in synchronism with the rear intermittent driving wheels 8. The front ends of the guide belts 47 are normally at the upper positions of the paths through which they move pivotally, to enable the transfer containers 17 to move in an arc. When an inner vessel 19 is discharged from a transfer container 17, the guide belts 47 are moved pivotally in the downward direction to their horizontal position to support the inner vessel 19 forced out of the transfer container 17, and transfer that inner vessel 19 onto the driving rollers 38 of the removal means 39. Referring to the drawings, reference numeral 49 denotes a cylinder for actuating the arm levers 48, and 50 an airtight switching means connecting the high-pressure sterilizing tank 1 and cooling tank 3 together.

The embodiment of the present invention is constructed as described above. Accordingly, an inner vessel 19 containing the materials being treated, which is transferred by the feed means 30 to a position behind the front intermittent driving wheels 8, is forcibly fitted into the transfer container 17 by the locking rods 35 of the insertion means 31 when the driving wheels 8 are stopped temporarily. The locking pawls 23 of the transfer container 17 then engages with the locking holes 24 in the inner vessel 19, so that the inner vessel 19 and transfer container 17 are combined unitarily with each other.

When the intermittent driving wheels 8 are then turned, the transfer container 17 is moved forward smoothly so that it enters the high-pressure tank 1 through the cooling tank 3 and airtight switching means 50. The materials are sterilized with hot water in the high-pressure tank 1. The transfer container 17 housing the sterilized materials therein is thereafter moved to the rear intermittent driving wheels 8 through the airtight switching means 50 and the cooling tanks 2, 3.

Consequently, the locking pawls 23 are disengaged from the locking holes 24 by the release guides 45, and, during one of the intermittent stoppages of the driving wheels 8, the pushers 44 are actuated to extend through the holes 26 and force the inner vessel 19 out of the transfer container 17 onto the removal means 39 via the guide belts 47. The inner vessel 19 is then transferred to a predetermined position by the removal means 39, while the transfer container 17 from which the inner vessel 19 has been moved is moved to the front intermittent driving wheels 8 again, so that another inner vessel 19 containing materials to be treated can be fitted thereinto.

While the transfer container 17 having a plurality of holes in the walls thereof passes through the hot water in the high-pressure sterilizing tank 1 and the cooling liquid in the cooling tanks 2, 3, the hot water or the cooling liquid flow from the through holes 18 in the transfer container 19 through the liquid flow passage a formed by the projections 25, to sterilize thermally or cool the materials being treated, in a uniform manner and at a high rate. While the front and rear intermittent driving wheels 8 are turned, the guide plates 37 and guide belts 47 are at the upper positions of the paths through which they move pivotally, so as not to hamper the movement of the transfer container 17. When the inner vessel 19 is either fitted into or forced out of the transfer container 17, the guide plates 37 and the guide belts 47 fall down to their horizontal positions to enable the inner vessel 19 to be introduced into the transfer container 17, or onto the removal means 39, smoothly and reliably.

In the above embodiment, guide plates are used as the guide members fitting the inner vessel 19 into the transfer container 17, and belts are used as guide members to permit a shortening of the stroke of the pushers 44 removing the inner vessel 19 from the transfer container 17. These guide members may, of course, be substituted by other equivalent means. Also the constructions of the insertion means and the discharge means are not limited to those described in the above embodiment.

As described above, the present invention is provided with a pair of transfer chains circulated through a high-pressure sterilizing tank and cooling tanks, transfer containers having openings at one side thereof and a plurality of holes in the walls thereof, which are supported between the transfer chains, open-topped inner vessels removably fitted into the transfer containers through the openings thereof, and locking members formed at both ends of each inner vessel, with which resilient locking means provided at both ends of each transfer container are detachably engaged. Accordingly, an inner vessel containing the materials to be treated can be inserted into and discharged from the transfer container easily and speedily by a single button-pressing operation. Since the top of the inner vessel is open, the materials being treated can be placed therein very easily. The inner vessel enables a large improvement in the sterilizing efficiency of the sterilizer of this kind. Since the materials being treated, which are placed in an inner vessel, can be inserted into a transfer container, the materials are not damaged during the insertion and discharge thereof into and from a transfer container. When an inner vessel consisting of a plurality of inner vessel members joined together, or an inner vessel having a plurality of compartments, is used, the wrapping and quality of a insecurely protected material, such as materials packed in inadequate bags, or smaller materials, are not damaged and spoiled. Thus, the sterilizing treatment can be carried out simply and reliably in an excellent manner.

A transfer container having a plurality of holes in the walls thereof and adapted to house materials which are being treated as it is transferred through a high-pressure sterizing tank and cooling tanks, is provided with projections supporting the materials, to enable the hot water and cooling liquid to spread around the materials speedily and uniformly via liquid flow passages defined by the projections. This allows the sterilizing and cooling efficiencies to be improved markedly. The projections also serve to prevent the displacement of the materials within the transfer container even if a reversing step is carried out during the movement of the transfer container along the chains. Since the thermal efficiency is high, it is unnecessary to heat the materials excessively. Therefore, no net-like burns occur on the pouches. Thus the materials can be sterilized continuously in an excellent manner at a high efficiency.

If the materials A being treated are moved backward as they are being transferred through the hot water tank and cooling tanks, the sterilized liquid is moved around the materials A so that the expansion pressure from the inside of the materials is applied to the outside thereof. This causes an increase in the friction between the materials and the projections 25, 25'. As a result, the materials A are not displaced, and the sterilizing and cooling effect can be further improved.

Since an inner vessel containing the materials is inserted into and discharged from a transfer container as the transfer container moves supported between a pair of transfer chains, and stops temporarily at the upper parts of a pair of front intermittent driving wheels and a pair of rear intermittent driving wheels, an inner vessel insertion means and an inner vessel discharge means can be provided easily near the opening of the transfer container. In addition, the guide members for the inner vessels are so provided that the guide members can be moved pivotally, i.e. fall down to a horizontal position between a transfer container and an inner vessel feed means, and between a transfer container and an inner vessel removal means, only when the inner vessel is being fitted into or discharged from the transfer container. Accordingly, the operation of moving the transfer containers is not hampered, and an inner vessel can be fitted into or discharged from a transfer container directly and smoothly without separating the transfer container from the main sterilizer unit. Therefore, an inner vessel containing the materials being treated in a continuous sterilizer of this kind can be inserted into and discharged from a transfer container automatically by very simply-constructed means. The present invention has such excellent effects.

The present invention is not, of course, limited to the above embodiment; it may be modified in various ways within the scope of the appended claims.

What is claimed is:

1. A sterilizer comprising:
    (a) a high-pressure sterilizing tank;
    (b) a cooling tank;
    (c) right and left transfer chain means positioned spaced apart to provide support for transfer containers therebetween and provided so as to circulate through said high-pressure sterilizing tank and said cooling tank;
    (d) a plurality of transfer containers wherein each of said transfer containers is supported between said transfer chain means, each of said transfer containers comprising two longitudinal end walls, a lateral side wall, a bottom wall, a top wall, and an open lateral side, each of said transfer containers having means defining a plurality of holes in said walls;
    (e) a plurality of inner vessels, each inner vessel comprising two longitudinal walls, two lateral side walls, a bottom wall, and an open top, each of said inner vessels being capable of containing materials to be sterilized, each of said inner vessels being removably insertable through said open lateral side in each of said transfer containers;
    (f) each of said inner vessels being provided with locking means at both longitudinal end walls thereof and each of said transfer containers being provided with resilient locking members at both longitudinal end walls thereof, said locking members being engageable with said locking means; and
    (g) an unlocking member provided at a portion of said sterilizer at which said inner vessels are discharged, said unlocking member provided to release said resilient locking members from engagement with said locking means of said inner vessels.

2. A sterilizer comprising:
    (a) a high-pressure sterilizing tank;
    (b) a cooling tank;
    (c) right and left transfer chain means positioned spaced apart to provide support for transfer containers therebetween and provided so as to circulate through said high-pressure sterilizing tank and said cooling tank;
    (d) transfer containers, each of said transfer containers comprising two longitudinal end walls, a bottom wall, a top wall, a lateral side wall and an open lateral side, each of said transfer containers being supported between said transfer chain means;
    (e) inner vessels, each of said inner vessels comprising two longitudinal end walls, two lateral side walls, a bottom wall and an open top and being provided with locking means at both longitudinal end walls thereof, each of said inner vessels being capable of containing materials to be sterilized, and each of said inner vessels being removably insertable into any of said transfer containers;
    (f) each of said transfer containers and each of said inner vessels having means defining a plurality of holes in the walls thereof, said holes having circumferential edges and projections extending from the circumferential edges, said projections being capable of supporting materials to be sterilized away from the inner surface of said transfer containers and said inner vessels, said projections defining liquid flow passages therebetween, each of said transfer containers being provided at both longitudinal end walls thereof with resilient locking members engageable with said locking means of said inner vessels; and,
    (g) an unlocking member provided at a portion of said sterilizer at which said inner vessels are discharged for releasing said resilient locking members from engagement with said locking means of said inner containers.

3. A sterilizer having
    (a) a high-pressure sterilizing tank,
    (b) a cooling tank,
    (c) right and left transfer chain means positioned spaced apart to provide support for transfer containers therebetween and provided so as to circulate through said high pressure sterilizing tank and said cooling tank;
    (d) transfer containers, each of said transfer containers being supported between said transfer chain means and each of said transfer containers having two longitudinal end walls, a lateral side wall, an open lateral side, a bottom wall, a top wall and means defining a plurality of holes in the walls thereof;
    (e) inner vessels, each of said inner vessels having two longitudinal end walls, two lateral side walls, a bottom wall and an open top, each of said inner vessels being capable of containing materials to be sterilized, each of said inner vessels having means defining a plurality of holes in the walls thereof and being provided with locking means at both longitudinal end walls thereof, each of said inner vessels being removably insertable through said open lateral side of said transfer containers, each of said transfer containers also being provided at both longitudinal end walls thereof with resilient locking members engageable with said locking means of said inner vessels; and (f) an inner vessel insertion and discharge means comprising parts of said transfer chain means, said parts of said transfer chain means being run around a pair of front intermittent-driving wheels and a pair of rear intermittent-driving wheels, said parts of said transfer chain means being slack in front of said front intermittent-driving wheels, behind said rear intermittent-driving wheels, and between said front and rear intermittent-driving wheels, an inner vessel insertion unit provided in front of said front intermittent-driving wheels for introducing an inner vessel from a feed means for supplying materials to be sterilized into said transfer containers, an unlocking member for releasing said resilient locking members from engagement with said locking means of said inner vessels, an inner vessel discharge unit for pushing said inner vessels out of said transfer containers onto a treated material removal means provided behind said rear intermittent-driving wheels, and inner vessel guide members being provided between said feed means and said front intermittent-driving wheels and between said treated material removal means and said rear intermittent-driving wheels.

4. A sterilizer having:
(a) a high-pressure sterilizing tank;
(b) a cooling tank;
(c) right and left transfer chain means positioned spaced apart to provide support for transfer containers therebetween and provided so as to circulate through said high pressure sterilizing tank and said cooling tank;
(d) transfer containers, each of said transfer containers being supported between said transfer chain means and each of said transfer containers having two longitudinal end walls, a lateral side wall, an open lateral side, a bottom wall, a top wall and means defining a plurality of holes in the walls thereof;
(e) inner vessels, each of said inner vessels having two longitudinal end walls, two lateral side walls, a bottom wall and an open top, each of said inner vessels being capable of containing materials to be sterilized, each of said inner vessels having means defining a plurality of holes in the walls thereof and being removably insertable through said open lateral side of said transfer containers; and (f) an inner vessel insertion and discharge means, said inner vessel insertion and discharge means including:
parts of said transfer chain means, said parts of said transfer chain means being run around a pair of front intermittent-driving wheels and a pair of rear intermittent-driving wheels, said parts of said transfer chain means being slack in front of said front intermittent-driving wheels, behind said rear intermittent-driving wheels, and between said front and rear intermittent-driving wheels; an inner vessel insertion unit provided in front of said front intermittent-driving wheels for introducing an inner vessel from a feed means for supplying materials to be sterilized into said transfer containers; an inner vessel discharge unit for pushing said inner vessels out of said transfer containers onto a treated material removal means provided behind said rear intermittent-driving wheels; and inner vessel guide members being provided between said feed means and said front intermittent-driving wheels, and between said treated material removal means and said rear intermittent-driving wheels.

5. A sterilizer according to claim 4, wherein each of said inner vessel guide members is formed pivotably, said guide members being moved pivotally to horizontal positions to guide an inner vessel only when the inner vessel is being inserted into or discharged from a transfer container.

6. A sterilizer according to claim 4, wherein each of said inner vessel guide members in the inner vessel insertion unit consists of right and left pivotable guide plates and each of said inner vessel guide members in the inner vessel discharge unit consisting of right and left pivotable guide belts.

* * * * *